US011116398B2

(12) United States Patent
Astigarraga et al.

(10) Patent No.: US 11,116,398 B2
(45) Date of Patent: Sep. 14, 2021

(54) DETECTION OF CONTAGIOUS DISEASES USING UNMANNED AERIAL VEHICLE

(71) Applicant: INTERNATIONAL BUSINESS MACHINES CORPORATION, Armonk, NY (US)

(72) Inventors: Tara Astigarraga, Fairport, NY (US); Christopher V. Derobertis, Hopewell Junction, NY (US); Louie A. Dickens, Tucson, AZ (US); Jose R. Mosqueda Mejia, Michoacan (MX); Daniel J. Winarski, Tucson, AZ (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 932 days.

(21) Appl. No.: 15/688,915

(22) Filed: Aug. 29, 2017

(65) Prior Publication Data
US 2019/0059724 A1 Feb. 28, 2019

(51) Int. Cl.
*A61B 5/00* (2006.01)
*G01S 7/04* (2006.01)
*H04N 21/4223* (2011.01)
*G16H 50/80* (2018.01)
*G05D 1/00* (2006.01)

(52) U.S. Cl.
CPC .............. *A61B 5/0002* (2013.01); *G01S 7/04* (2013.01); *G16H 50/80* (2018.01); *H04N 21/4223* (2013.01); *B64C 2201/088* (2013.01); *G05D 1/00* (2013.01)

(58) Field of Classification Search
None
See application file for complete search history.

(56) References Cited

U.S. PATENT DOCUMENTS

| 7,073,748 | B2 | 7/2006 | Maurer et al. |
| 8,442,700 | B2 | 5/2013 | Anderson |
| 2016/0070261 | A1 | 3/2016 | Heilman et al. |

FOREIGN PATENT DOCUMENTS

| CN | 104699111 A | 6/2015 |
| KR | 20160092538 A | 8/2016 |
| WO | 2015132208 A1 | 9/2015 |

OTHER PUBLICATIONS

Watts, Adam C., et al. "Small unmanned aircraft systems for low-altitude aerial surveys." The Journal of Wildlife Management 74.7 (2010): 1614-1619 (Year: 2010).*
Wang, Hai. Design of a Drone-Assisted Wireless Sensor Network System for Feedlot Animal Health Monitoring. MS thesis. Graduate Studies, 2015. (Year: 2015).*
Nyum KR20160092538A as also cited on the Aug. 29, 2017 IDS but here with full Google English translation (Year: 2016).*
Barrett, M. A., et al. "Big Data and Disease Prevention: From Quanitifed Self to Quanitified Communities", Sep. 2013, Big Data, vol. 1, No. 3, pp. 168-175.
Callaghan, Meaghan Lee, "CDC Releases Plan to Control Zika in the U.S.", Popular Science, Jun. 15, 2016; http://www.popsci.com; 1 pg.
Engelking, Carl "Drones Could Help Prevent Future Disease Outbreaks" Discover Magazine; Drone 360; dated Jun. 11, 2015; http://blogs.discovermagazine.com/drone360/2015/06/11/drones-could-help-prevent-future . . . ; 2 pgs.
Joseph, Andrew "STAT CDC preparing to deploy strike teams to limit spread of Zika", dated Jun. 14, 2016; 2017 STAT; https://www.statnews.com/2016/06/14/cdc-zika-local-response/; retrieved from Internet Mar. 8, 2017, p. 1-3.
Liesa "Image Recognition—Introducing Image Recognition: The Future of Social Listening", "presented by talkwalker.com Blog; dated Mar. 9, 2016; https://www.talkwalker.com/blog/introducing-image-recognition-the-future-of-social-listening/"; 9 pgs.
New York Department of Environment Conservation "Reporting Dead Wildlife", retrieved from Internet: http://www.dec.ny.gov/animals/6957.html; Mar. 10, 2017, 3 pgs.
Christiansen, Peter et al. "Automated Detection and Recognition of Wildlife Using Thermal Cameras", Sensors 2014, 14, doi: 10.3390/140813778; www.mdpi.com/journal/sensors; pp. 13778-13793.

* cited by examiner

*Primary Examiner* — G Steven Vanni
(74) *Attorney, Agent, or Firm* — Cantor Colburn LLP; Steven Chiu

(57) ABSTRACT

Methods, systems and computer program products for detecting contagious diseases in a wildlife population using a drone are provided. Aspects include monitoring, by a drone, a geographic area and capture images of the geographic area and analyzing the captured images to identify a deceased wildlife in a region of the geographic area. Aspects also include performing increased monitoring of the region and capture supplemental images of the region using the drone and analyzing the supplemental images to identify a number of deceased wildlife in the region. Based on a determination that number of deceased wildlife in the region, greater than a threshold number, a corrective action is taken.

20 Claims, 7 Drawing Sheets

DETECTION OF CONTAGIOUS DISEASES USING UNMANNED AERIAL VEHICLE

BACKGROUND

The present invention relates generally to systems, methods, and computer program products for detecting contagious diseases and, more specifically, to detecting contagious diseases in wildlife populations using an unmanned aerial vehicle.

The spread of contagious diseases in wildlife populations poses various risks to humans including the risk of the disease being spread to humans. The spread of contagious diseases in wildlife populations can be detected by the presence of an abnormally large number of deceased wildlife in an area. Currently, there are no standard methods of reporting or monitor deceased wildlife. Rather, the reporting of deceased wildlife is an opt-in, best-effort, manual action that is at best sporadically performed by people.

SUMMARY

Embodiments include computer-implemented methods and computer program products for detecting contagious diseases in wildlife populations using an unmanned aerial vehicle. The method includes monitoring, by a drone, a geographic area and capturing images of the geographic area and analyzing the captured images to identify a deceased wildlife in a region of the geographic area. The method also includes performing increased monitoring of the region and capture supplemental images of the region using the drone and analyzing the supplemental images to identify a number of deceased wildlife in the region. Based on a determination that number of deceased wildlife in the region greater than a threshold number, a corrective action is taken.

Embodiments also include a drone for detecting contagious diseases in a wildlife population. The drone includes a memory and a processor communicatively coupled to the memory, wherein the processor is configured to monitor a geographic area and capture images of the geographic area and analyze the captured images to identify a deceased wildlife in a region of the geographic area. The processor is further configured to perform increased monitoring of the region and capture supplemental images of the region using the drone and analyze the supplemental images to identify a number of deceased wildlife in the region. Based on a determination that number of deceased wildlife in the region greater than a threshold number, the processor takes a corrective action.

Additional features are realized through the techniques of the present invention. Other embodiments and aspects of the invention are described in detail herein and are considered a part of the claimed invention. For a better understanding of the invention with the features, refer to the description and to the drawings.

BRIEF DESCRIPTION OF THE DRAWINGS

The subject matter which is regarded as the invention is particularly pointed out and distinctly claimed in the claims at the conclusion of the specification. The foregoing and other features of embodiments of the invention are apparent from the following detailed description taken in conjunction with the accompanying drawings in which:

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two or three digit reference numbers. With minor exceptions, the leftmost digit(s) of each reference number correspond to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

Embodiments include systems, methods and computer program products for detecting contagious diseases in wildlife populations using an unmanned aerial vehicle. In exemplary embodiments, an unmanned aerial vehicle is configured to monitor a geographic area for the presence of a deceased wildlife. Once a deceased wildlife is detected, the drone performs increased monitoring of the region in which the deceased wildlife was located. In one embodiment, based on determining that a number of deceased wildlife in the region exceed a threshold value the unmanned aerial vehicle can create an alert that includes the location of the deceased wildlife and one or more images of the deceased wildlife. In another embodiment, based on determining that a number of deceased wildlife in the region exceed a threshold value the unmanned aerial vehicle can collect a sample from one of the deceased wildlife and take the sample to another location for testing.

Figure 1:
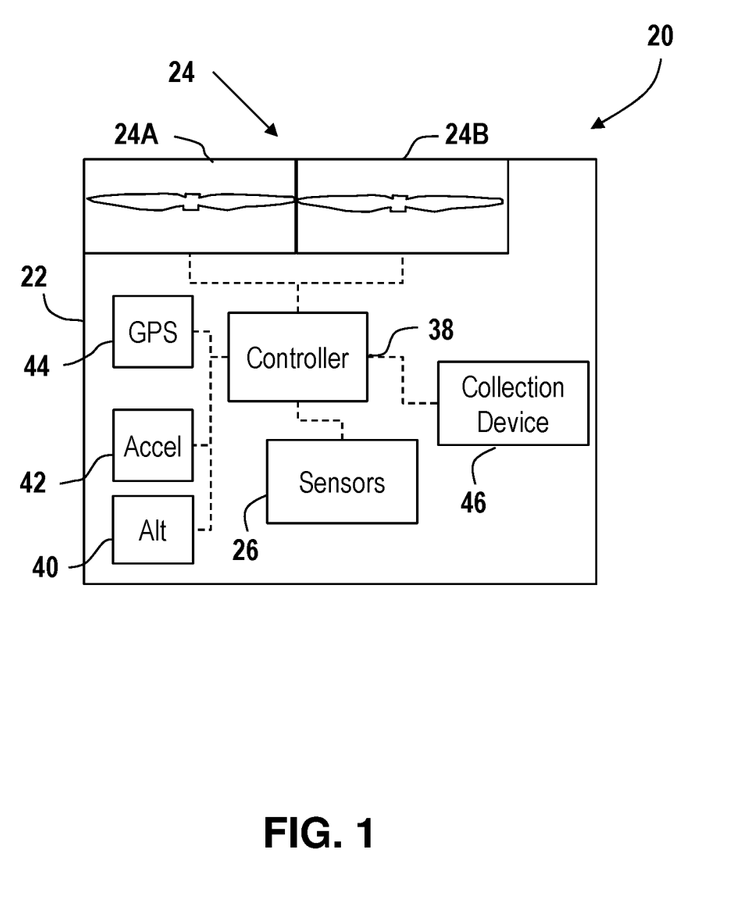
FIG. 1 depicts a block diagram of an unmanned aerial vehicle in accordance with an embodiment of the present invention.

Referring now to FIG. 1, an embodiment is shown of a drone 20 or unmanned aerial vehicle. As used herein, the term "drone" refers to an aerial vehicle capable of operating autonomously from a human operator to perform a predetermined function. The drone 20 includes a fuselage 22 that supports at least one thrust device 24. In an embodiment, the drone 20 includes a plurality of thrust devices 24A, 24B, such as four thrust devices arranged about the periphery of the fuselage 22. In an embodiment, the thrust devices 24 include propeller member that rotates to produce thrust. The thrust devices 24 may be configurable to provide both lift (vertical thrust) and lateral thrust (horizontal thrust). The vertical and horizontal components of the thrust allow the changing of the altitude, lateral movement and orientation (attitude) of the drone 20.

In the exemplary embodiment, the fuselage 22 and thrust devices 24 are sized and configured to carry a plurality of sensors 26. In exemplary embodiments, the sensors 26 can include image capture equipment, video capture equipment, audio capture equipment, depth capture equipment, or any other type of data capture equipment. In one embodiment, the sensors 26 include a camera, an inferred camera, and one or more gas sensors. In some embodiments, the sensors can include a variety of chemical sensors configured to detect the presence of specific compounds. For example, the gas sensors can be configured to detect compounds that are associated with decomposing wildlife, such as sulfur dioxide, methane, benzene derivatives and long chain hydrocarbons.

The drone 20 includes a controller 38 having a processing circuit. The controller 38 may include processors that are responsive to operation control methods embodied in application code such as those shown in FIGS. 4 and 5. These methods are embodied in computer instructions written to be executed by the processor, such as in the form of software. The controller 38 is coupled transmit and receive signals from the thrust devices 24 to determine and change their operational states (for example adjust lift from thrust devices 24). The controller 38 may further be coupled to one or more devices that enable to the controller to determine the position, orientation, and altitude of the drone 20. In an embodiment, these devices include an altimeter 40, a gyroscope or accelerometers 42 or a global positioning satellite (GPS) system 44. The controller 38 is further coupled to the one or more sensors 26. In exemplary embodiments, the drone 20 is configured to simultaneously detect the presence a chemical compound, such as the methane gas, while recording its GPS location.

In exemplary embodiments, the drone 20 includes a camera that captures images that are processed with photogrammetry tools to develop a three-dimensional model of the environment the drone is flying in. Such model can be stereographic imaging of an object from images acquired by a single camera under different viewing angle and altitudes.

In exemplary embodiments, the controller 38 of the drone 20 is configured to analyze images captured by the camera(s) to identify wildlife present in the images. In one embodiment, the controller 38 can use information from the gas sensors, the infrared cameras, or from previously stored images to determine if the wildlife present in the images is likely deceased.

In exemplary embodiments, the drone 20 includes a collection device 46 that is configured to collect a sample of a deceased wildlife identified by the drone. The collection device 46 is controlled by the controller 38 and can be configured to collect an entire deceased wildlife or to take a sample of the deceased wildlife. In exemplary embodiments, the collection device 46 is designed to prevent further spreading of any contagious disease that the deceased wildlife may have by the drone 20. For example, the collection device 46 can include a scoop that retrieves the deceased wildlife and places it into a sealed bag and a sanitization mechanism that sanitizes the drone 20 after collecting the deceased wildlife, or a sample of it. In one embodiment, the collection device 46 can include a fumigant on the drone 20 that kills the fleas on captured deceased wildlife, so the drone 20 does not inadvertently act as an agent and spread the diseases borne by the deceased wildlife.

Figure 2:
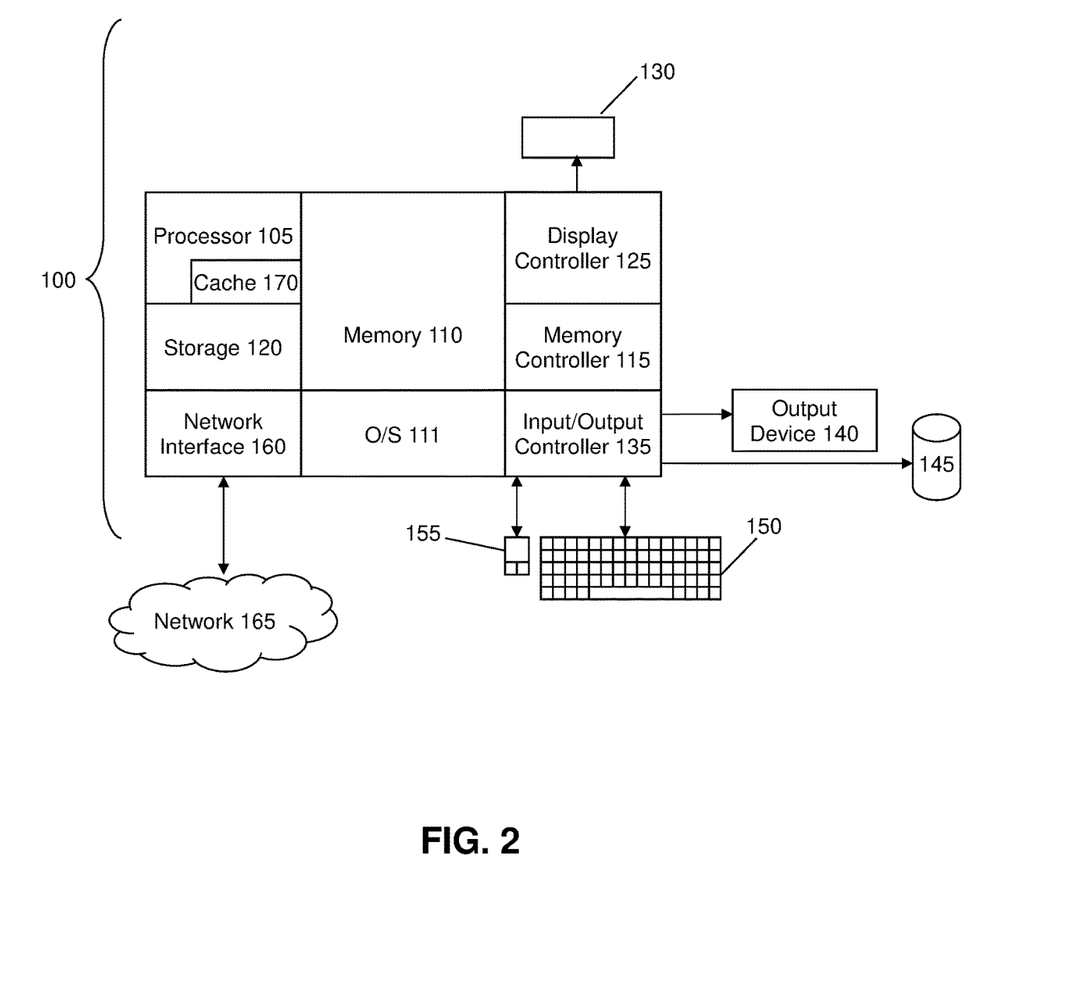
FIG. 2 depicts a block diagram of a controller for an unmanned aerial vehicle in accordance with an embodiment of the present invention.

FIG. 2 illustrates a block diagram of a controller 100 for use in implementing a system or method according to some embodiments. The systems and methods described herein may be implemented in hardware, software (e.g., firmware), or a combination thereof. In some embodiments, the methods described may be implemented, at least in part, in hardware and may be part of the microprocessor of a special or general-purpose controller 38, such as a personal computer, workstation, minicomputer, or mainframe computer.

In some embodiments, as shown in FIG. 2, the controller 100 includes a processor 105, memory 110 coupled to a memory controller 115, and one or more input devices 145 and/or output devices 140, such as peripheral or control devices that are communicatively coupled via a local I/O controller 135. These devices 140 and 145 may include, for example, battery sensors, position sensors, cameras, microphones and the like. Input devices such as a conventional keyboard 150 and mouse 155 may be coupled to the I/O controller. The I/O controller 135 may be, for example, one or more buses or other wired or wireless connections, as are known in the art. The I/O controller 135 may have additional elements, which are omitted for simplicity, such as controllers, buffers (caches), drivers, repeaters, and receivers, to enable communications.

The I/O devices 140, 145 may further include devices that communicate both inputs and outputs, for instance disk and tape storage, a network interface card (NIC) or modulator/demodulator (for accessing other files, devices, systems, or a network), a radio frequency (RF) or other transceiver, a telephonic interface, a bridge, a router, and the like.

The processor 105 is a hardware device for executing hardware instructions or software, particularly those stored in memory 110. The processor 105 may be a custom made or commercially available processor, a central processing unit (CPU), an auxiliary processor among several processors associated with the controller 38, a semiconductor based microprocessor (in the form of a microchip or chip set), a macroprocessor, or other device for executing instructions. The processor 105 includes a cache 170 that can be organized as a hierarchy of more cache levels (L1, L2, etc.).

The memory 110 may include one or combinations of volatile memory elements (e.g., random access memory, RAM, such as DRAM, SRAM, SDRAM, etc.) and nonvolatile memory elements (e.g., ROM, erasable programmable read only memory (EPROM), electronically erasable programmable read only memory (EEPROM), programmable read-only memory (PROM), tape, compact disc read only memory (CD-ROM), disk, diskette, cartridge, cassette or the like, etc.). Moreover, the memory 110 may incorporate electronic, magnetic, optical, or other types of storage media. Note that the memory 110 may have a distributed architecture, where various components are situated remote from one another but may be accessed by the processor 105.

The instructions in memory 110 may include one or more separate programs, each of which comprises an ordered listing of executable instructions for implementing logical functions. In the example of FIG. 2, the instructions in the memory 110 include a suitable operating system (OS) 111. The operating system 111 essentially may control the execution of other computer programs and provides scheduling, input-output control, file and data management, memory management, and communication control and related services.

Additional data, including, for example, instructions for the processor 105 or other retrievable information, may be stored in storage 120, which may be a storage device such as a hard disk drive or solid state drive. The stored instructions in memory 110 or in storage 120 may include those enabling the processor to execute one or more aspects of the systems and methods of this disclosure.

The controller 100 may further include a display controller 125 coupled to a user interface or display 130. In some embodiments, the display 130 may be an LCD screen. In some embodiments, the controller 100 may further include a network interface 160 for coupling to a network 165. The network 165 may be an IP-based network for communication between the controller 38 and an external server, client and the like via a broadband connection. The network 165 transmits and receives data between the controller 38 and external systems. In an embodiment, the external system may be the UAV 20. In some embodiments, the network 165 may be a managed IP network administered by a service provider. The network 165 may be implemented in a wireless fashion, e.g., using wireless protocols and technologies, such as WiFi, WiMax, satellite, etc. The network 165 may also be a packet-switched network such as a local area network, wide area network, metropolitan area network, the Internet, or other similar type of network environment. The network 165 may be a fixed wireless network, a wireless local area network (LAN), a wireless wide area network (WAN) a personal area network (PAN), a virtual private network (VPN), intranet or other suitable network system and may include equipment for receiving and transmitting signals.

Systems and methods according to this disclosure may be embodied, in whole or in part, in computer program products or in controller 100, such as that illustrated in FIG. 2.

Figure 3:
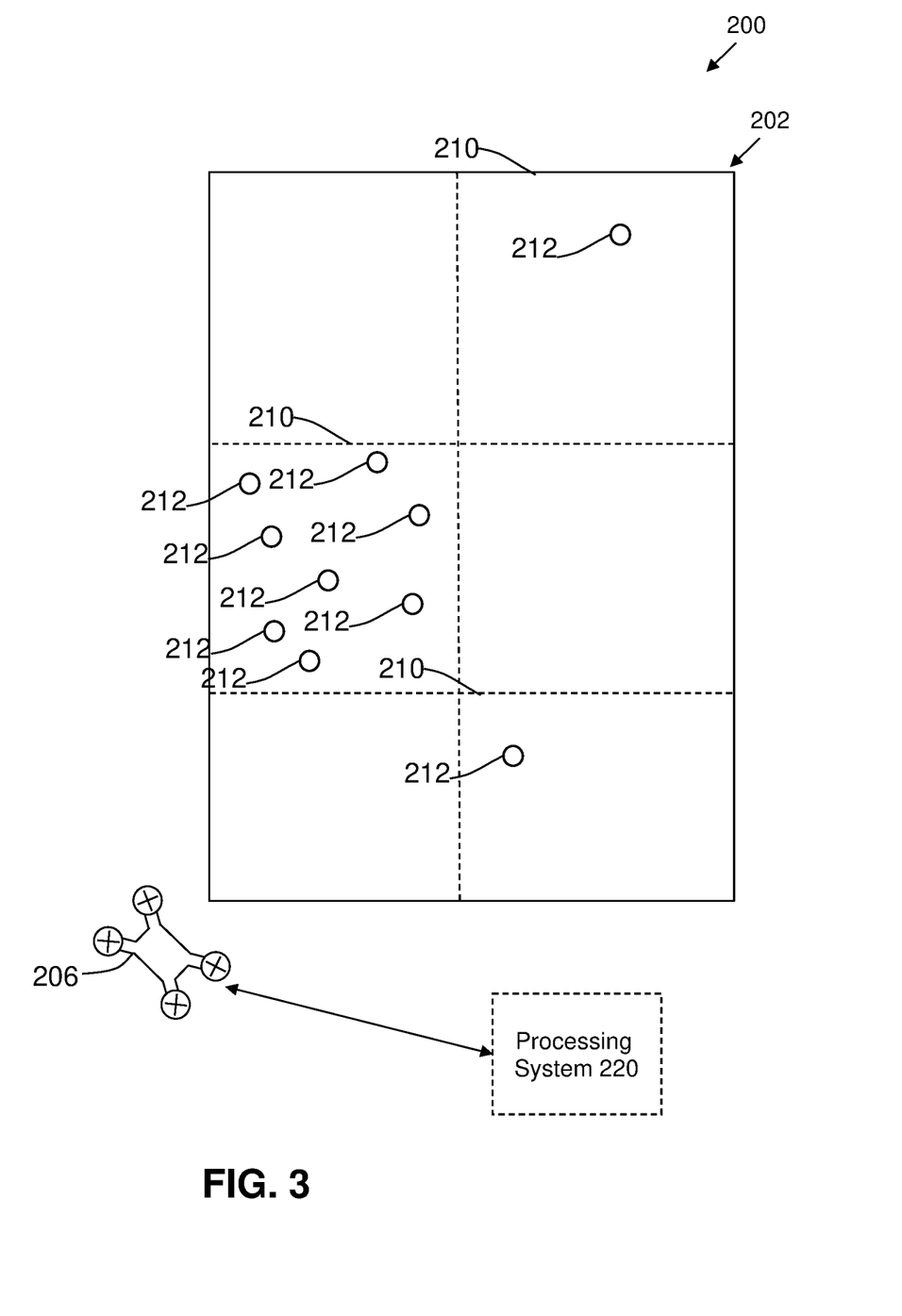
FIG. 3 depicts a plan view of a system for detecting contagious diseases using unmanned aerial vehicles in accordance with an embodiment of the present invention.

Referring now to FIG. 3, a plan view of a system 200 for detecting contagious diseases in wildlife populations using a drone 206 in accordance with an embodiment is shown. In exemplary embodiments, a processing system 220, such as the one shown in FIG. 2, is configured to communicate with the drone 206. In exemplary embodiments, the drones 206 are configured to monitor a geographic area 202 for the presence of deceased wildlife 212. In exemplary embodiments, the geographic area is divided into a plurality of regions 210 and the regions 210 that include one or more deceased wildlife 212 are subjected to increased monitoring by the drone 206.

In exemplary embodiments, once a drone 206 identifies a deceased wildlife 212 in a region 210, the drone 206 captures an image of the deceased wildlife 212 and records the time and location at which the deceased wildlife 212 was identified. The drone 206 can report this information to the processing system 220 or it may store this data locally. In exemplary embodiments, the drone 206 is configured to increase the frequency at which it monitors the region 210 for a time period after the detection of the deceased wildlife 212. For example, if the drone 206 identifies a deceased bird in an area that it is configured to monitor on a weekly basis, the drone 206 may perform daily monitoring of that area on a daily basis for the next ten days. If the number of additional deceased birds identified in the area does not exceed a threshold value, the monitoring can revert to a weekly basis. However, if the number of additional deceased birds identified in the area does exceed the threshold value, the drone 206 can take various actions to report the information and/or collect samples from the deceased birds.

Figure 4:
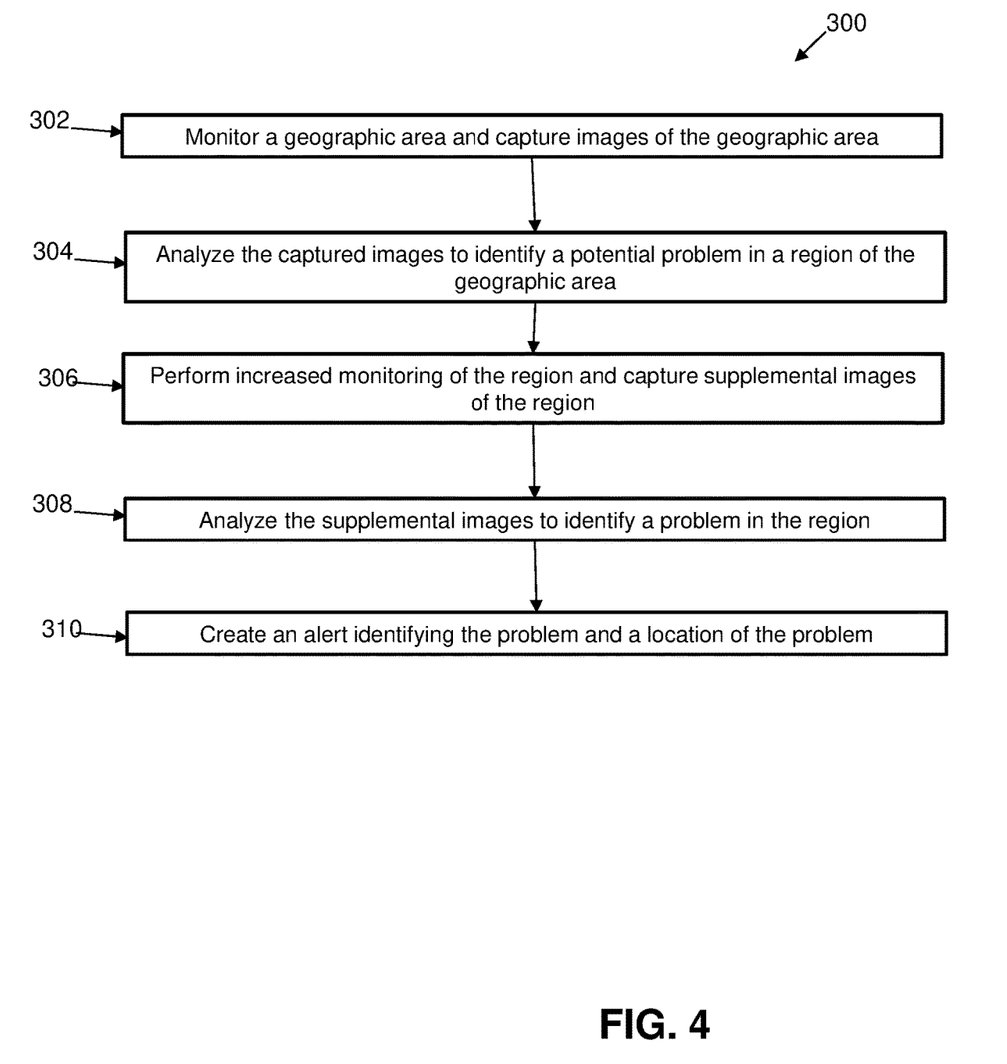
FIG. 4 depicts a flow diagram of a method detecting contagious diseases using unmanned aerial vehicles in accordance with an embodiment of the present invention.

Referring now to FIG.4, a flow diagram of a method 300 detecting contagious diseases in wildlife populations using a drone is depicted. As shown at block 302, the method 300 includes monitoring a geographic area and capturing images of the geographic area. Next, as shown at block 304, the method 300 includes analyzing the captured images to identify a potential problem in a region of the geographic area. In exemplary embodiments, analyzing the captured images can include performing automated analysis of the captured images to identify wildlife and determining if the identified wildlife is likely deceased by comparing the imaged to previously captured images, by analyzing the condition of the wildlife, by analyzing thermal images of the wildlife captured by an infrared camera, or the like.

In exemplary embodiments, the determination that a region of the geographic area includes a potential problem can be based on a number of deceased wildlife that are identified in the regions. The potential problem determination can be based on wildlife specific thresholds. For example, one deceased bear may be sufficient to denote a potential problem while less than five deceased birds in an area may not be sufficient to denote a potential problem. The threshold values for denoting a potential problem can be defined by a system administrator.

Next, as shown at block 306, the method 300 includes performing increased monitoring of the region and capture supplemental images of the region. In exemplary embodiments, the increased monitoring of the region can include capturing supplemental images of the region more frequently, i.e., daily versus weekly, and/or capturing supplemental images of the region at a higher level of detail, i.e., capturing higher resolution images of the region. The method 300 also includes analyzing the supplemental images to identify a problem in the region, as shown at block 308. In exemplary embodiments, the determination that a region of the geographic area includes a problem can be based on a number of deceased wildlife that are identified in the regions. The problem determination can be based on wildlife specific thresholds that are similar to the potential problem thresholds, but which have higher values. Next, as shown at block 310, the method 300 includes creating an alert identifying the problem and a location of the problem. In exemplary embodiments, the alert is transmitted to a processing system along with one or more images of the identified deceased wildlife. The images can include geotag information that identifies the GPS coordinates of the area depicted in the images.

Figure 5:
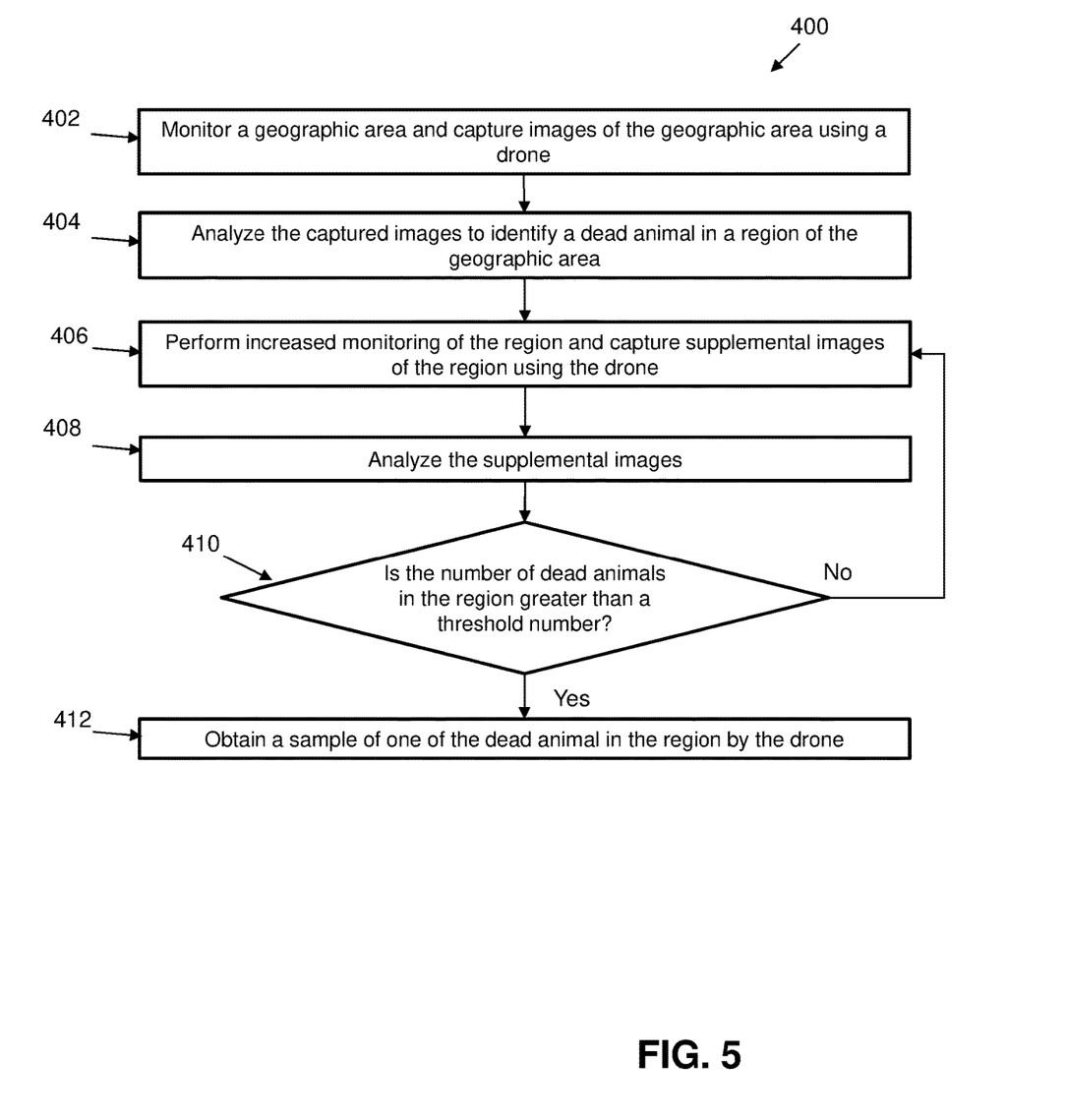
FIG. 5 depicts a flow diagram of a method for detecting contagious diseases using unmanned aerial vehicles in accordance with an another embodiment of the present invention.

Referring now to FIG. 5, a flow diagram of a method 400 detecting contagious diseases in wildlife populations using a drone is depicted. As shown at block 402, the method 400 includes monitoring a geographic area and capture images of the geographic area using a drone. Next, as shown at block 404, the method includes analyzing the captured images to identify a deceased wildlife in a region of the geographic area. In exemplary embodiments, analyzing the captured images can include performing automated analysis of the captured images to identify wildlife and determining if the identified wildlife is likely deceased by comparing the imaged to previously captured images, by analyzing the condition of the wildlife, by analyzing thermal images of the wildlife captured by an infrared camera, or the like.

The method 400 also includes perform increased monitoring of the region and capture supplemental images of the region using the drone, as shown at block 406. In exemplary embodiments, the increased monitoring of the region can include capturing supplemental images of the region more frequently, and/or capturing supplemental images of the region at a higher level of detail. Next, at block 408, the supplemental images are analyzed. In exemplary embodiments, analyzing the supplemental images can include performing automated analysis of the captured images to identify wildlife and determining if the identified wildlife is likely deceased by comparing the imaged to previously captured images, by analyzing the condition of the wildlife, by analyzing thermal images of the wildlife captured by an infrared camera, or the like. At decision block 410, it is determined if the number of deceased wildlife in a given region is above a threshold number. In one example, it is determined if there are more than ten deceased birds in any one square mile. If the number of deceased wildlife in a given region is above a threshold number, the method proceeds to block 412 and the drone obtains a sample from one or more of the deceased wildlife that can be tested to identify any contagious diseases the wildlife may have had. Otherwise, the method 400 returns to block 406 and continues to perform increased monitoring of the region. In exemplary embodiments, the increased monitoring of the region is continued for a specific time period from the initial detection of one or more deceased wildlife in the regions.

In one embodiment, a drone is equipped with visual scanners that are configured to detect deceased wildlife to record the GPS location of each of the deceased wildlife identified. The drone includes a processor that calculates the number of deceased wildlife in an area and the location density of the deceased wildlife, i.e., the number of deceased wildlife per square mile. If the number of deceased wildlife per square mile is above a first threshold the area can be identified as having a potential problem and if the number of deceased wildlife per square mile is above a second threshold, which is higher than the first, the area can be identified as having a problem and a corrective action can be taken. In exemplary embodiments, the thresholds could be defined based on specific wildlife, i.e. number of birds, fishes, etc.

It should be appreciated that while embodiments herein refer to a controller 100 for controlling and managing the drone, this is for exemplary purposes and the claims should not be so limited. In other embodiments, the controlling and managing of the drone may be performed by a plurality of controllers, a distributed computing environment or a cloud computing environment. It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 6:
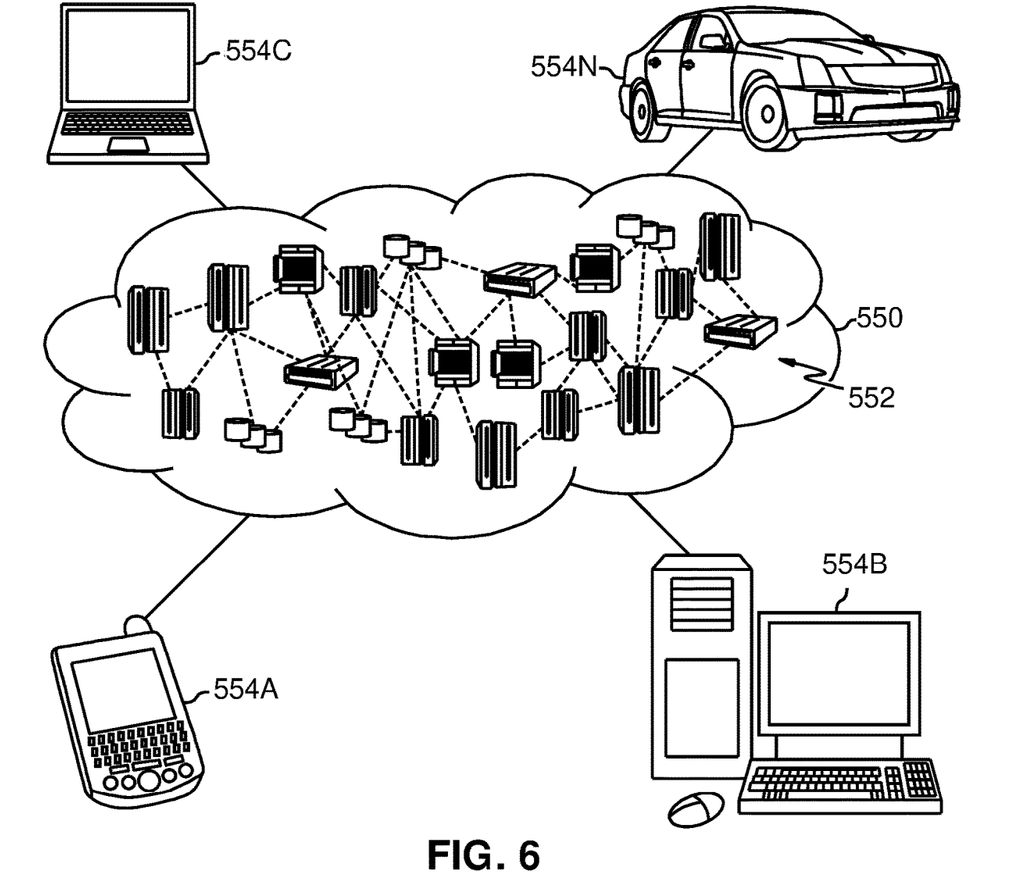
FIG. 6 depicts a cloud computing environment according to an embodiment of the present invention.

Referring now to FIG. 6, illustrative cloud computing environment 550 is depicted. As shown, cloud computing environment 550 comprises one or more cloud computing nodes 552 with which local computing devices used by cloud consumers, such as, for example, personal digital assistant (PDA) or cellular telephone 554A, desktop computer 554B, laptop computer 554C, and/or automobile computer system 554N may communicate. Nodes 552 may communicate with one another. They may be grouped (not shown) physically or virtually, in one or more networks, such as Private, Community, Public, or Hybrid clouds as described hereinabove, or a combination thereof. This allows cloud computing environment 550 to offer infrastructure, platforms and/or software as services for which a cloud consumer does not need to maintain resources on a local computing device. It is understood that the types of computing devices 554A-N shown in FIG. 6 are intended to be illustrative only and that computing nodes 552 and cloud computing environment 550 can communicate with any type of computerized device over any type of network and/or network addressable connection (e.g., using a web browser).

Figure 7:
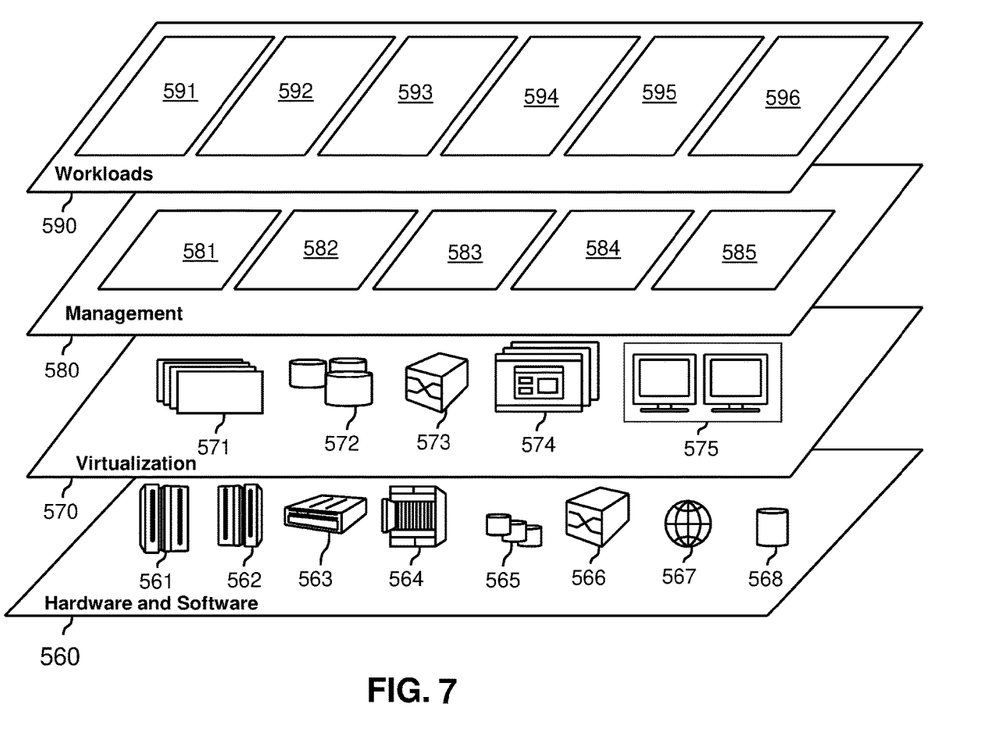
FIG. 7 depicts abstraction model layers according to an embodiment of the present invention.

Referring now to FIG. 7, a set of functional abstraction layers provided by cloud computing environment 550 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 560 includes hardware and software components. Examples of hardware components include: mainframes 561; RISC (Reduced Instruction Set Computer) architecture based servers 562; servers 563; blade servers 564; storage devices 565; and networks and networking components 566. In some embodiments, software components include network application server software 567 and database software 568.

Virtualization layer 570 provides an abstraction layer from which the following examples of virtual entities may be provided: virtual servers 571; virtual storage 572; virtual networks 573, including virtual private networks; virtual applications and operating systems 574; and virtual clients 575.

In one example, management layer 580 may provide the functions described below. Resource provisioning 581 provides dynamic procurement of computing resources and other resources that are utilized to perform tasks within the cloud computing environment. Metering and Pricing 582 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 583 provides access to the cloud computing environment for consumers and system administrators. Service level management 584 provides cloud computing resource allocation and management such that required service levels are met. Service Level Agreement (SLA) planning and fulfillment 585 provides pre-arrangement for, and procurement of, cloud computing resources for which a future requirement is anticipated in accordance with an SLA.

Workloads layer 590 provides examples of functionality for which the cloud computing environment may be utilized. Examples of workloads and functions which may be provided from this layer include: mapping and navigation 591; software development and lifecycle management 592; virtual classroom education delivery 593; data analytics processing 594; transaction processing 595; and a UAV positioning and monitoring management 596. The UAV positioning and monitoring management 596 may perform one or more methods for detecting contagious diseases using unmanned aerial vehicles, such as but not limited to the methods described in reference to FIGS. 4 and 5 for example.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting-data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:
1. A computer-implemented method comprising:
monitoring, by a drone, a geographic area and capturing images of the geographic area;
analyzing the captured images to identify deceased wildlife in a region of the geographic area;

performing increased monitoring of the region and capturing supplemental images of the region using the drone;

analyzing the supplemental images to identify a number of deceased wildlife in the region; and if a determination that the number of deceased wildlife in the region is greater than a threshold number, then taking a corrective action.

2. The method of claim 1, wherein the corrective action includes obtaining a sample of one of the deceased wildlife in the region by the drone.

3. The method of claim 1, wherein the corrective action includes creating an alert which includes the number of deceased wildlife, a location of the region, and at least one of the supplemental images.

4. The method of claim 1, wherein the increased monitoring of the region is performed for a period of time from the identification of the deceased wildlife in the region.

5. The method of claim 1, wherein the increased monitoring of the region includes increasing a frequency at which the drone captures images of the region.

6. The method of claim 1, wherein the increased monitoring of the region includes increasing a resolution of the images which the drone captures of the region.

7. The method of claim 1, wherein the threshold number is determined at least in part by a type of the wildlife.

8. A drone comprising:

a memory comprising a computer readable storage medium having program instructions embodied therewith;

a processor communicatively coupled to the memory, wherein the program instructions are configured to cause the processor to perform:

monitor a geographic area and capture images of the geographic area;

analyze the captured images to identify deceased wildlife in a region of the geographic area;

perform increased monitoring of the region and capture supplemental images of the region using the drone;

analyze the supplemental images to identify a number of deceased wildlife in the region; and if a determination that the number of deceased wildlife in the region is greater than a threshold number, then take a corrective action.

9. The drone of claim 8, wherein the corrective action includes obtaining a sample of one of the deceased wildlife in the region by the drone.

10. The drone of claim 8, wherein the corrective action includes creating an alert which includes the number of deceased wildlife, a location of the region, and at least one of the supplemental images.

11. The drone of claim 8, wherein the increased monitoring of the region is performed for a period of time from the identification of the deceased wildlife in the region.

12. The drone of claim 8, wherein the increased monitoring of the region includes increasing a frequency at which the drone captures images of the region.

13. The drone of claim 8, wherein the increased monitoring of the region includes increasing a resolution of the images which the drone captures of the region.

14. The drone of claim 8, wherein the threshold number is determined at least in part by a type of the wildlife.

15. A computer program product comprising a non-transitory computer readable storage medium having program instructions embodied therewith, the program instructions executable by a processor to cause the processor to perform a method comprising:

monitoring, by a drone, a geographic area and capturing images of the geographic area;

analyzing the captured images to identify deceased wildlife in a region of the geographic area;

performing increased monitoring of the region and capturing supplemental images of the region using the drone;

analyzing the supplemental images to identify a number of deceased wildlife in the region; and if a determination that the number of deceased wildlife in the region is greater than a threshold number, then taking a corrective action.

16. The computer program product of claim 15, wherein the corrective action includes obtaining a sample of one of the deceased wildlife in the region by the drone.

17. The computer program product of claim 15, wherein the corrective action includes creating an alert which includes the number of deceased wildlife, a location of the region, and at least one of the supplemental images.

18. The computer program product of claim 15, wherein the increased monitoring of the region is performed for a period of time from the identification of the deceased wildlife in the region.

19. The computer program product of claim 15, wherein the increased monitoring of the region includes increasing a frequency at which the drone captures images of the region.

20. The computer program product of claim 15, wherein the increased monitoring of the region includes increasing a resolution of the images which the drone captures of the region.

* * * * *